US00PP35526P2

(12) United States Plant Patent
Hartman

(10) Patent No.: US PP35,526 P2
(45) Date of Patent: Dec. 5, 2023

(54) ***CALADIUM* PLANT NAMED 'FRH OF15-107'**

(50) Latin Name: ***Caladium* X *hortulanum***
Varietal Denomination: FRH OF15-107

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/121,507

(22) Filed: Mar. 14, 2023

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
CPC ..... A01H 5/12; A01H 5/00; A01H 6/10
See application file for complete search history.

(56) References Cited

U.S. PATENT DOCUMENTS

PP27,071 P2 * 8/2016 Hartman ..... A01H 5/12 Plt./373
PP32,602 P2 * 12/2020 Hartman ..... A01H 1/121 Plt./373

* cited by examiner

*Primary Examiner* — June Hwu
(74) *Attorney, Agent, or Firm* — C. Anne Whealy

(57) ABSTRACT

A new and distinct cultivar of *Caladium* plant named 'FRH OF15-107', characterized by its short to intermediate in height and mounding plant habit; dense, leafy and bushy appearance; vigorous growth habit and rapid growth rate; fancy-type leaves that are dark green in color with dark red-colored centers; first emerging leaves are glossy and later emerging leaves are duller in luster; and petioles that are reddish pink in color with dense brownish green-colored streaks.

4 Drawing Sheets

Figure 1:
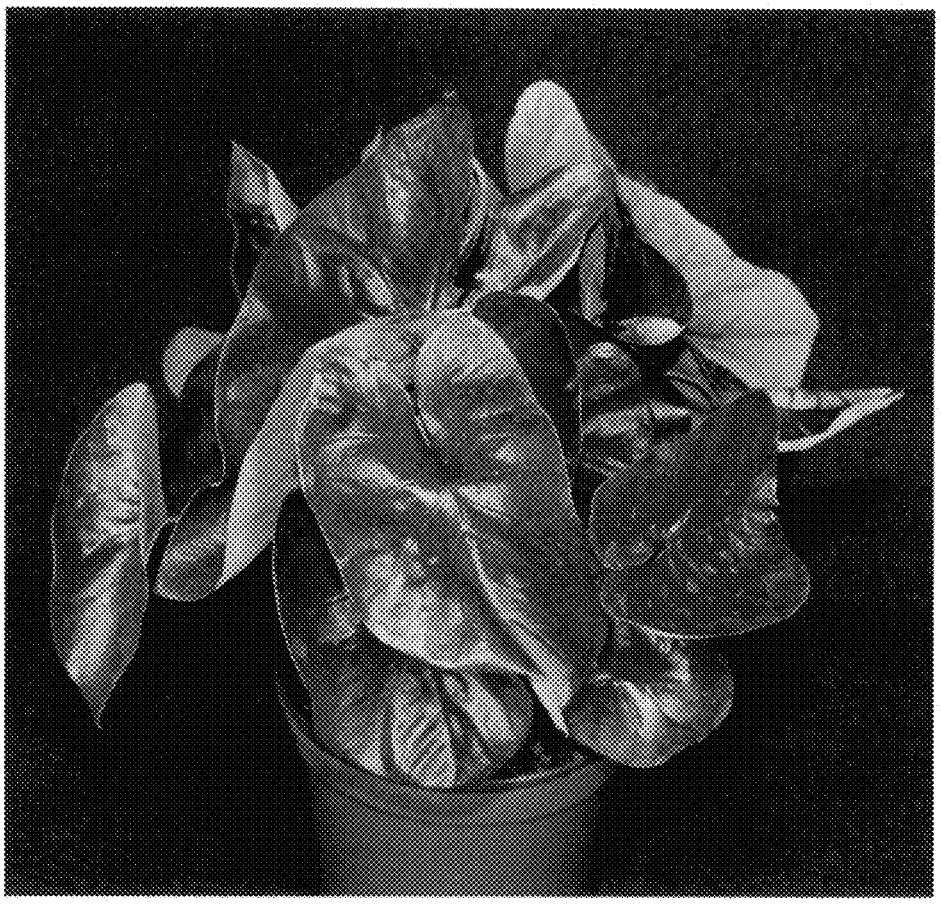

Botanical designation: *Caladium* X *hortulanum.*
Cultivar denomination: 'FRH OF15-107'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum,* commercially referred to as a fancy leaf-type *Caladium* and hereinafter referred to by the name 'FRH OF15-107'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2014 in Avon Park, Fla. of *Caladium* X *hortulanum* 'UF 4424', disclosed in U.S. Plant Pat. No. 25,598, as the female, or seed, parent with *Caladium* X *hortulanum* 'Red Flash', not patented, as the male, or pollen, parent. The new *Caladium* plant was discovered and selected by the Inventor as a single plant within the progeny of the stated cross-pollination in a controlled outdoor nursery environment in Avon Park, Fla. in September, 2015.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2016 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'FRH OF15-107'. These characteristics in combination distinguish 'FRH OF15-107' as a new and distinct *Caladium* plant:

1. Short to intermediate in height and mounding plant habit; dense, leafy and bushy appearance.
2. Vigorous growth habit and rapid growth rate.
3. Fancy-type leaves that are dark green in color with dark red-colored centers.
4. First emerging leaves are glossy and later emerging leaves are duller in luster.

5. Petioles that are reddish pink in color with dense brownish green-colored streaks.

Plants of the new *Caladium* differ primarily from plants of the female parent, 'UF 4424', in the following characteristics:

1. Plants of the new *Caladium* are short to intermediate in height whereas plants of 'UF 4424' are short in height.
2. Leaves of plants of the new *Caladium* are dark green in color with dark red-colored centers whereas leaves of plants of 'UF 4424' are dark red in color with narrow green-colored margins.
3. Leaf petioles of plants of the new *Caladium* are reddish pink in color with dense brownish green-colored streaks whereas leaf petioles of plants of 'UF 4424' are greyed red in color.

Plants of the new *Caladium* differ primarily from plants of the male parent, 'Red Flash', in the following characteristics:

1. Plants of the new *Caladium* are shorter than plants of 'Red Flash'.
2. Plants of the new *Caladium* are more mounding than and not as upright as plants of 'Red Flash'.
3. Plants of the new *Caladium* produce finished plants in 15-cm containers about two to three weeks earlier than plants of 'Red Flash'.
4. Leaves of plants of the new *Caladium* are dark green in color with dark red-colored centers whereas leaves of plants of 'Red Flash' have red-colored venation and intervenous areas with pink and white-colored spots and dark green-colored borders.
5. Leaf petioles of plants of the new *Caladium* are reddish pink in color with dense brownish green-colored streaks whereas leaf petioles of plants of 'Red Flash' are reddish pink to tannish pink in color with darker-colored stippling and stripes.

Plants of the new *Caladium* can be compared to plants of *Caladium* X *hortulanum* 'Frieda Hemple', not patented. In side-by-side comparisons, plants of the new *Caladium* differ primarily from plants of 'Frieda Hemple' in the following characteristics:

1. Plants of the new *Caladium* are shorter than plants of 'Frieda Hemple'.
2. Plants of the new *Caladium* are more mounding than and not as upright as plants of 'Frieda Hemple'.
3. Leaves of plants of the new *Caladium* are dark green in color with dark red-colored centers whereas leaves of plants of 'Frieda Hemple' are medium green in color with bright red-colored centers and venation.
4. First emerged leaves of plants of the new *Caladium* are glossy whereas first emerged leaves of plants of 'Frieda Hemple' are dull in sheen.
5. Leaf petioles of plants of the new *Caladium* are reddish pink in color with dense brownish green-colored streaks whereas leaf petioles of plants of 'Frieda Hemple' are tannish pink in color with dense brownish black-colored stippling and streaks.

Plants of the new *Caladium* can also be compared to plants of *Caladium* X *hortulanum* 'Bombshell', disclosed in U.S. Plant Pat. No. 23,817. In side-by-side comparisons, plants of the new *Caladium* differ primarily from plants of 'Bombshell' in the following characteristics:

1. Plants of the new *Caladium* are shorter than plants of 'Bombshell'.
2. Plants of the new *Caladium* are more mounding than and not as upright as plants of 'Bombshell'.
3. Plants of the new *Caladium* produce finished plants in 15-cm containers about two weeks earlier than plants of 'Bombshell'.
4. Leaves of plants of the new *Caladium* are dark green in color with dark red-colored centers whereas leaves of plants of 'Bombshell' have dark red to greyed purple-colored venation and intervenous areas surrounded with dark green-colored borders.
5. Leaf petioles of plants of the new *Caladium* are reddish pink in color with dense brownish green-colored streaks whereas leaf petioles of plants of 'Bombshell' are tannish pink in color with black-colored stippling.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'FRH OF15-107' grown in a container that has had its tuber de-eyed prior to planting.

Figure 2:
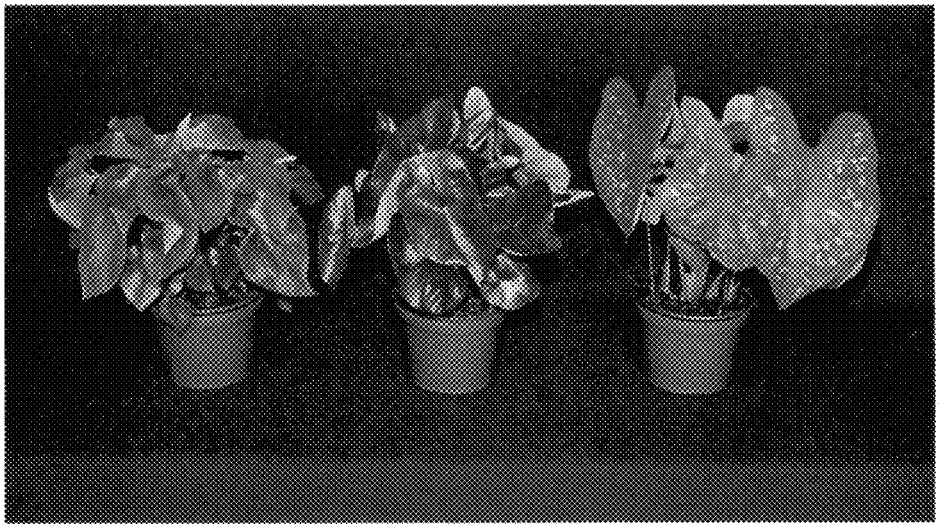

The photograph at the top of the second sheet (FIG. 2) is side perspective view of typical plants of the female parent, 'UF 4424' (left), 'FRH OF15-107' (center) and the male parent, 'Red Flash' (right).

Figure 3:
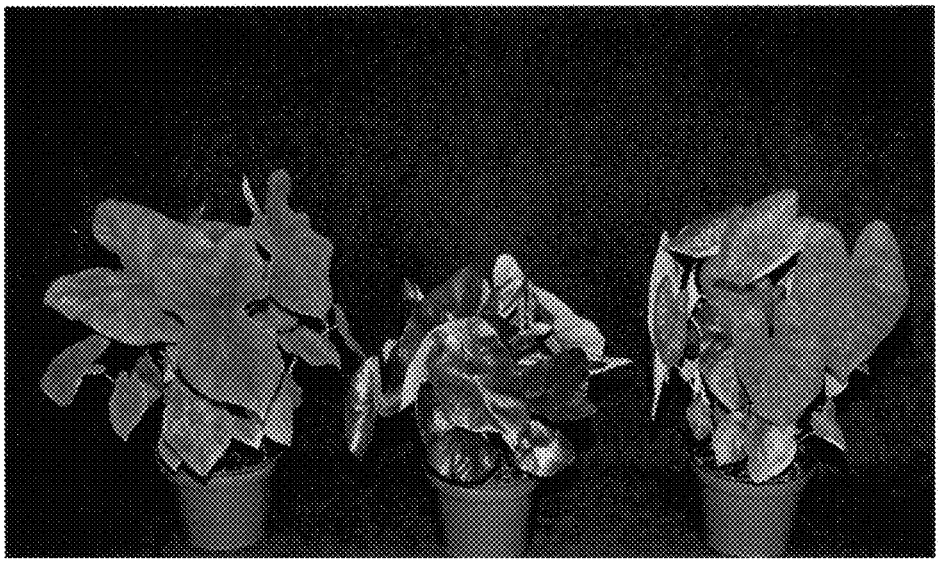

The photograph at the bottom of the second sheet (FIG. 3) is side perspective view of typical plants of 'Frieda Hemple' (left), 'FRH OF15-107' (center) and 'Bombshell' (right).

Figure 4:
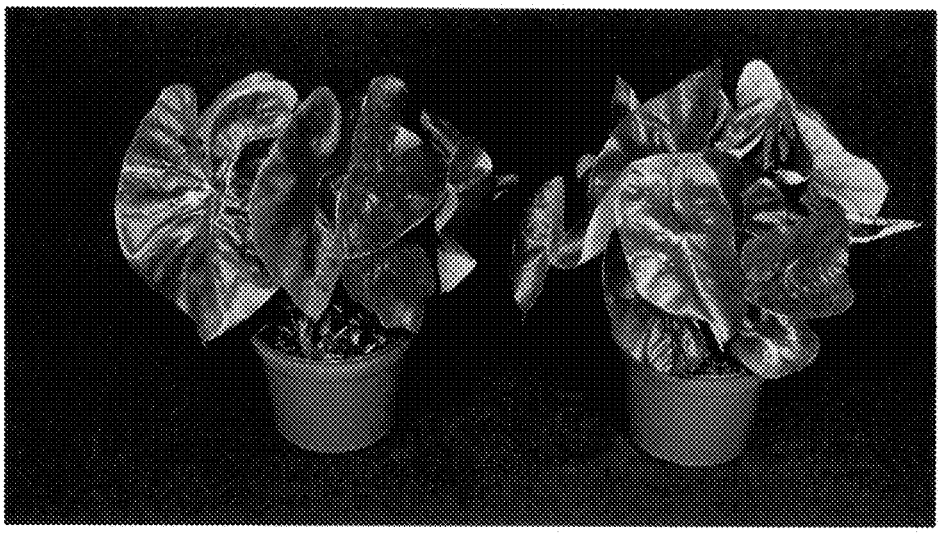

The photograph at the top of the third sheet (FIG. 4) is a comparison view of typical plants of 'FRH OF15-107' grown in containers, the plant on the left has not had its tuber de-eyed and the plant on the right has had its tuber de-eyed prior to planting.

Figure 5:
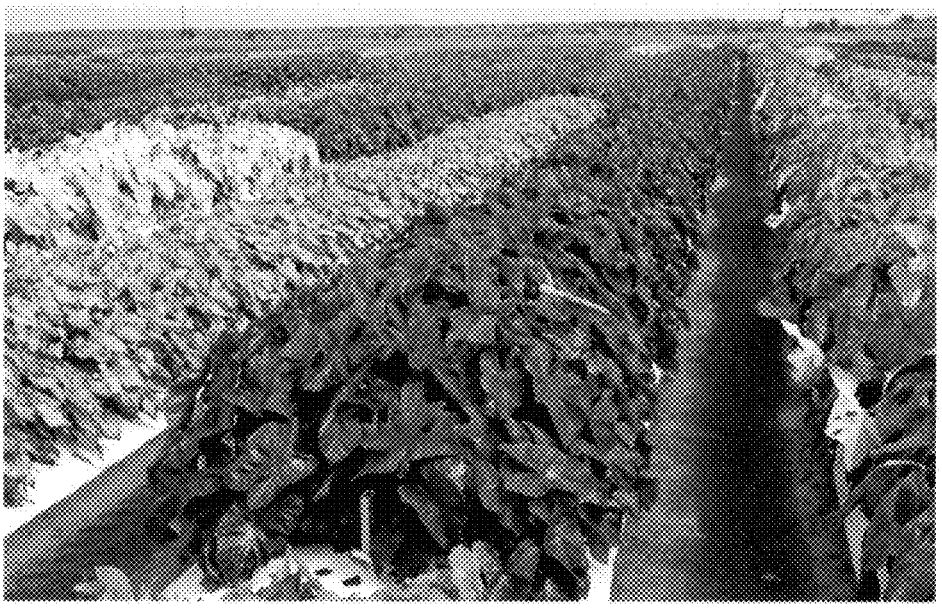

The photograph at the bottom of the third sheet (FIG. 5) is a side perspective view of typical plants of 'FRH OF15-107' grown in an open production field.

Figure 6:
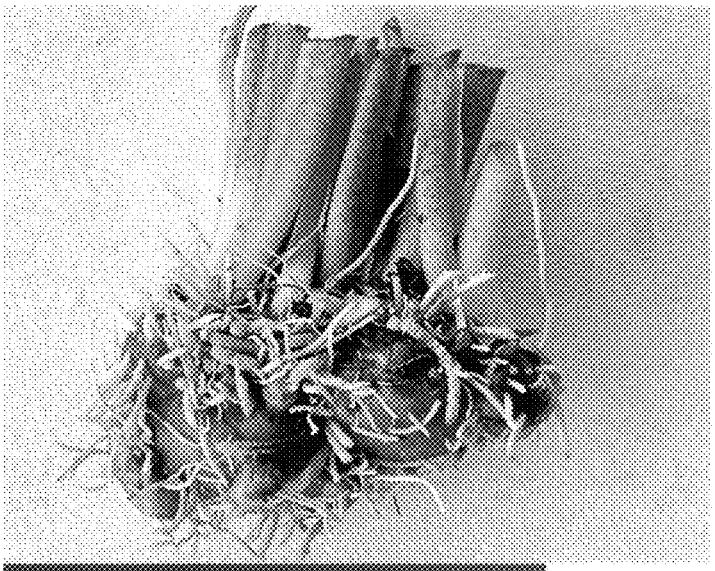

The photograph at the top of the fourth sheet (FIG. 6) is a close-up view of typical freshly-harvested tubers with roots and leaf petioles of 'FRH OF15-107'.

Figure 7:
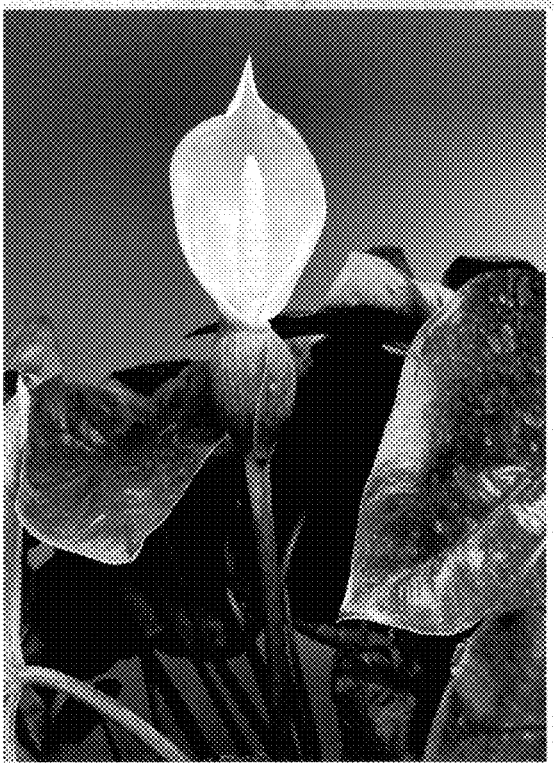

The photograph at the bottom of the fourth sheet (FIG. 7) is a close-up view of a typical inflorescence of 'FRH OF15-107'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28C to 33C, night temperatures ranged from about 22C to 25C and light levels were about 1,300 μmol. During the production of the outdoor nursery-grown plants, day temperatures ranged from about 29C to 35C, night temperatures ranged from about 23C to 26C and full sunlight conditions. Plants grown in the shade house were six weeks old and plants grown in the outdoor nursery were six months old when the photographs and the detailed description were taken. In the following description, color references are made to The Royal Horticultural Society Colour Chart, 2001 and 2015 Editions, except where general tetms of ordinary dictionary significance are used.

Botanical classification: *Caladium* X *hortulanum* 'FRH OF15-107'.

Parentage:

*Female, or seed, parent.*—*Caladium* X *hortulanum* 'UF 4424', disclosed in U.S. Plant Pat. No. 25,598.

*Male, or pollen, parent.*—*Caladium* X *hortulanum* 'Red Flash', not patented.

Propagation:

*Type.*—By "chipping" the tubers.

*Time to initiate roots, summer.*—About seven to ten days at temperatures about 32C.

*Time to initiate roots, winter.*—About two to three weeks at temperatures about 24C.

*Tuber description* (*outdoor nursery-grown plants*).—Appearance: Multi-segmented; individual segments are ovate to irregular in shape. Height: About 3.7 cm. Diameter: About 5.5 cm to 8.5 cm. Segment height: About 2.6 cm to 3 cm. Segment diameter: About 3.5 cm to 3.7 cm. Axillary bud shape: Roughly triangular. Axillary bud height: About 5.5 mm. Axillary bud width: About 7 mm. Texture: Thick, starchy; somewhat brittle. Color: Periderm, freshly-harvested: Close to 199A with specks, close to N199B. Periderm, dried: Close to 200A. Epidermis: Close to N170D becoming closer to 159A tinged with close to N170D with subsequent development. Cortical tissue: Close to 8D. Axillary buds: Close to 38B and 49B. Root description: Thick, fleshy contractile roots with few lateral branches; color, close to NN155D tinged with close to 59D; actual color of the roots is dependent on substrate composition, water quality, fertilizer type and formulation, substrate temperature and physiological age of roots. Rooting density: Dense.

Plant description:

*Plant type.*—Herbaceous perennial; suitable as a potted plant in containers 15-cm to 25-cm and suitable as a landscape plant in shaded areas.

*Plant and growth habit.*—Short to intermediate in height and mounding plant habit; dense, leafy and bushy appearance; very vigorous growth habit and rapid growth rate; potted plants finish in saleable form in about four to six weeks after planting tubers; leaf petioles and leaves arise from one or more growing points on tubers; leaf petioles initially upright and leaning outwardly with development.

*Plant height, from soil level to top of foliar plane, shade house-grown potted plants.*—When de-eyed, about 20 cm to 23 cm; when not de-eyed, about 27 cm to 29.5 cm.

*Plant height, from soil level to top of floral plane, shade house-grown potted plants.*—About 30 cm.

*Plant diameter, shade house-grown potted plants.*—When de-eyed, about 22 cm to 28 cm; when not de-eyed, about 25 cm to 26 cm.

*Number of shoots per plant, shade house-grown potted plants, tubers not de-eyed.*—About four to five develop per #1 tuber.

*Number of shoots per plant, shade house-grown potted plants, tubers de-eyed.*—About five to eight develop per #1 tuber.

*Cataphylls, shade house-grown potted plants.*—Length: About 6.5 cm to 10 cm. Width: About 1 cm to 1.2 cm. Shape: Linear to wedge-shaped. Apex: Acute to emarginate. Base: Sheathing the stem. Texture, outer and inner surfaces: Smooth, glabrous. Color, outer surface: Close to 182D densely streaked, stippled and flushed with close to 200B to 200C; color becoming closer to 199A and when dried, close to 200B to 200C, with subsequent development. Color, inner surface: Close to N170D with colors and color patterns visible from outer surface.

Leaf description:

*Arrangement and type.*—Alternate; simple; fancy-type.

*Length, shade house-grown potted plants.*—When de-eyed, about 14 cm to 19 cm; when not de-eyed, about 15.5 cm to 21.2 cm.

*Width, shade house-grown potted plants.*—When de-eyed, about 8 cm to 11.2 cm and flattened, about 8.2 cm to 11.8 cm; when not de-eyed, about 9.5 cm to 11 cm and flattened, about 9.8 cm to 13.2 cm

*Shape.*—Ovate to cordate.

*Apex.*—Variable, acuminate, acute to cuspidate.

*Base.*—Sagittate-peltate; cordate.

*Margin.*—Entire; mostly flat to somewhat wavy with broad undulations.

*Texture and luster, upper surface.*—Mostly smooth to somewhat rugose, glabrous; medium thickness; first emerged leaves are glossy and later emerged leaves are dull in sheen.

*Texture and luster, lower surface.*—Mostly smooth to somewhat rugose, glabrous; glaucous and dull in sheen.

*Venation pattern.*—Pinnate and palmate.

*Color, shade house-grown potted de-eyed plants.*—When developing and fully expanded leaves, upper surface: Background color: Close to NN137A. Center: Close to 53A. Margins: Close to NN137A; edges, close to 183A. Basal notch: Close to 187A. Midvein: Close to 53A and 187B; areas surrounding veins, close to N45C and 53A. Lateral venation: Close to 53A, 187A and 187B; areas surrounding veins, close to N45C and 53A. When developing and fully expanded leaves, lower surface: Background color: Close to 191A and 191B. Center: Close to 46A tinged with close to 187C. Margins: Close to 191A and 191B; edges, close to 183A. Basal notch: Close to 187A. Midvein and primary veins: Close to 46A tinged with close to 187C; small veins, close to 187A.

*Color, shade house-grown potted not de-eyed plants.*—When developing and fully expanded leaves, upper surface: Background color: Close to 147A and 148A. Center: Close to 53A. Margins: Close to 147A and 148A; edges, close to 183A. Basal notch: Close to 187A. Midvein: Close to 53A; areas surrounding veins, close to 53A and 53B. Lateral venation: Close to 53A tinged with close to 187B; areas surrounding veins, close to 53A and 53B; small veins, close to 53A and 187A. When developing and fully expanded leaves, lower surface: Background color: Close to 148B. Center: Close to 46A and close to 46A tinged with close to 187C. Margins: Close to 148B; edges, close to 183A. Basal notch: Close to 187A. Midvein: Close to 46A. Lateral venation: Close to 46A and N187B; small veins, close to 187A.

*Petioles.*—Aspect: Initially upright and straight, and outwardly leaning with development; flexible. Length, shade house-grown de-eyed potted plants: About 17.5 cm to 21 cm. Length, shade house-grown not de-eyed potted plants: About 21 cm to 24.5 cm. Diameter, distally, shade house-grown de-eyed potted plants: About 3.5 mm to 5.5 mm. Diameter, distally, shade house-grown not de-eyed potted plants: About 4 mm to 5.5 mm. Diameter, proximally, shade house-grown de-eyed potted plants: About 6 mm. Diameter, proximally, shade house-grown not de-eyed potted plants: About 5.5 mm to 7 mm. Texture and luster: Smooth, glabrous and glaucous. Color, shade house-grown potted plants: Close to 182A and proximally, close to 182C; densely streaked and tessellated with close to 200A; just below the leaf junction, close to 60A streaked with close to 182A and 182D. Wing length, shade house-grown potted plants: About 5 cm to 6.4 cm. Wing diameter, shade house-grown potted plants: About 5 mm to 7 mm. Texture and luster, inner and outer surfaces: Smooth, glabrous; dull sheen. Wing color, shade house-grown potted plants: Outer surface: Close to 56C and N170D streaked, stippled and tessellated with close to 200A; may be tinged with close to N199A. Inner surface: Close to N155B, N170D and 56C; colors and patterns on the outer surface are visible on the inner surface.

Inflorescence description:

*Inflorescence arrangement.*—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance.*—Night-fragrant; jasmine-like with mint/camphor note.

*Natural flowering season and flower longevity.*—Plants of the new *Caladium* typically flower during the spring and summer in central Florida; flowers develop about eight weeks after growth commences; inflorescences last about three days before fading; inflorescences persistent.

*Spathe.*—Length, overall: About 10.5 cm. Length, distal open portion: About 6.7 cm. Length, proximal closed portion: About 3.8 cm. Width, distal open portion: About 3.8 cm. Depth, distal open portion: About 2 cm. Width, at constriction: About 1.3 cm. Width, proximal closed portion: About 2.2 cm. Shape, open portion: Broadly elliptic to slightly obovate. Apex: Acuminate. Base: Acute. Margin: Entire. Texture and luster, front surface: Smooth, glabrous; satiny sheen. Texture and luster, rear surface: Distally, smooth, glabrous with a dull sheen; proximally, smooth, glabrous, slightly glaucous with a satiny sheen. Color, front surface: Distal open portion: Close to NN155D; with subsequent development, becoming closer to 199B and 200C. Proximal closed portion: Close to 148D and 155C flushed with close to 187B to 187C; towards the base, flushed with close to 187A; color does not change with subsequent development. Color, rear surface: Distal open portion: Close to 145D and 157B; color does not change with subsequent development. Proximal closed portion: Close to 185A and 183A with streaks, close to 147B; color does not change with subsequent development.

*Spadix.*—Length, overall: About 6.7 cm. Length, male flower zone: About 3.5 cm. Length, sterile zone: About 2 cm. Length, female flower zone: About 1.2 cm. Diameter, male flower zone: About 7 mm. Diameter, sterile flower zone: About 5 mm. Diameter, female flower zone: About 6 mm. Shape: Columnar, spindle-shaped. Apex: Acute. Base: Obtuse. Aspect: Upright. Color, mature, male zone: Close to 158D. Color, mature, sterile zone: Close to 155D. Color, mature, female zone: Close to 159D and 158B. Male flowers: Quantity per spadix: About 130. Shape: Obovate. Height: About 3.5 mm. Diameter: About 3 mm. Pollen amount: Sparse. Pollen color: Close to 10C. Female flowers: Quantity per spadix: About 45. Shape: Obovate. Height: About 2.5 mm. Diameter: About 2 mm. Stigma color: Close to 159D. Ovary color: Close to 158B.

*Scapes.*—Length: About 19.5 cm. Diameter: About 5 mm. Strength: Sturdy; somewhat flexible. Aspect: Mostly erect, straight. Texture and luster: Smooth, glabrous; slightly glossy; just below spathe, slightly glaucous. Color: Close to 148B flushed with close to 200C, and stippled, streaked and tessellated with close to 200B to 200C; just below spathe, close to 147B to 147C, flushed with close to 184C and streaked with close to 185A.

*Seeds and fruits.*—To date, seed and fruit development have not been observed on plants of the new *Caladium.*

Pathogen tolerance/resistance: Plants of the new *Caladium* have been observed to have average tolerance to *Pythium* Root Rot and average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7C to about 40C and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'FRH OF15-107' as illustrated and described.

* * * * *